United States Patent [19]
Fujikura et al.

[11] Patent Number: 5,104,851
[45] Date of Patent: Apr. 14, 1992

[54] 2-(ALKYL-CYCLO)-1-PROPANOL, A PROCESS FOR PREPARING THE SAME AND PERFUMERY COMPOSITION CONTAINING THE SAME

[75] Inventors: Yoshiaki Fujikura, Utsunomiya; Hiroaki Ohnuma, Ichikai; Manabu Fujita, Kashiwa; Nao Toi, Sakura, all of Japan

[73] Assignee: Kao Corporation, Tokyo, Japan

[21] Appl. No.: 646,450

[22] Filed: Jan. 25, 1991

Related U.S. Application Data

[63] Continuation of Ser. No. 307,969, Feb. 9, 1989, abandoned.

[30] Foreign Application Priority Data

Feb. 10, 1988 [JP] Japan .................. 63-29937

[51] Int. Cl.$^5$ .............................. A61K 7/46
[52] U.S. Cl. ..................... 512/14; 512/22; 568/816; 568/822; 568/819; 252/174.11
[58] Field of Search ............. 512/14, 22; 252/174.11; 568/816, 822, 819

[56] References Cited

U.S. PATENT DOCUMENTS

| | | | |
|---|---|---|---|
| 2,029,618 | 2/1936 | Hopff | 568/822 |
| 3,024,287 | 3/1962 | Kennedy et al. | 568/822 |
| 3,075,881 | 1/1963 | Nordmann | 568/822 |
| 3,109,863 | 11/1963 | Bo et al. | 568/822 |
| 4,818,747 | 4/1989 | Giersch et al. | 512/14 |

FOREIGN PATENT DOCUMENTS

| | | | |
|---|---|---|---|
| 2707340 | 2/1977 | Fed. Rep. of Germany | 568/822 |
| 59-225134 | 12/1984 | Japan | 568/822 |
| 652113 | 5/1982 | Switzerland | 568/822 |
| 656609 | 7/1986 | Switzerland | 512/22 |

OTHER PUBLICATIONS

Searles, J.A.C.S., vol. 73, pp. 124–125 (1951).
Sadykhov et al, Chem. Abst., vol. 64, #8049b (1966).
Houben–Weyl Methoden der Organischen Chemie, 4th edition, vol. VI/Ia, part 2, 1980, Georg Thieme Press, Stuttgart pp. 1407–1409.
Beilsteins Handbuch der Organischen Chemie, 4th edition, vol. 6, 2nd supplement, 1944, Springer Press, Berlin, p. 57, lines 49–55, p. 39 . . . .

Primary Examiner—James H. Reamer
Attorney, Agent, or Firm—Oblon, Spivak, McClelland, Maier & Neustadt

[57] ABSTRACT

A 2-(alkyl-cyclohexyl)-1-propanol is disclosed. The compound is represented by formula (I):

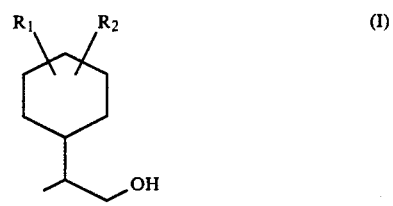

wherein $R_1$ and $R_2$ individually represent a group selected from the members consisting of methyl-, ethyl-, n-propyl-, i-propyl-, t-butyl-, and sec-butyl groups, provided that the total carbon atoms of the $R_1$ and $R_2$ groups are 4 to 7; either $R_1$ and $R_2$ is a hydrogen atom, the other being a cyclohexyl group; or $R_1$ and $R_2$ together form a hexamethylene ring together with 2 carbon atoms in the cyclohexane ring. The compound possesses a long-lasting, woody, floral odor, and can be widely used as perfumery materials such as perfumes, soaps, shampoos, aromatic goods, and detergents.

4 Claims, No Drawings

2-(ALKYL-CYCLO)-1-PROPANOL, A PROCESS FOR PREPARING THE SAME AND PERFUMERY COMPOSITION CONTAINING THE SAME

This application is a continuation of application Ser. No. 307,969, filed on Feb. 9, 1989, now abandoned.

BACKGROUND OF THE INVENTION

1. Field of the Invention

This invention relates to novel 2-(alkyl-cyclohexyl)-1-propanols, a process for preparing the same, and a perfumery composition comprising such a 2-(alkyl-cyclohexyl)-1-propanol.

2. Description of the Background

Several perfumery compounds belonging to 2-(alkyl-cyclohexyl)-1-propanols are conventionally known in the art. For instance, 2-(4-isopropyl-1-cyclohexyl)-1-propanol is known to impart a rosy, balsamic, mild, floral, woody odor (S. Arctendar; Perfume and Flavor Chemicals) and 2-(4-tertbutyl-1-cyclohexyl)-1-propanol is known to provide a musky, woody, sandal odor (Swiss Patent No. 652,113). Because of their highly volatile nature, these compounds are used primarily as a top- or middle note. No compound which can provide tenacity and can be used as a base note is known.

Materials used as a base note in the preparation of perfumes are very important because of their basic function of characterizing the types of fragrance. Among these base note materials, those providing tenacious, woody, floral odor are mainly from naturally occurring substances such as vetiverol. Since vetiverol is an expensive material, the development of a novel synthetic perfumery compound similar to vetiverol in its fragrance has been desired.

In view of this situation, the present inventors have undertaken extensive studies. As a result, the inventors found that 2-(alkyl-cyclohexyl)-1-propanols can provide a long-lasting woody, floral odor, and that the odor is very similar to that imparted by naturally occurring substances when these are formulated in a perfumery composition.

SUMMARY OF THE INVENTION

Accordingly, an object of this invention is to provide 2-(alkyl-cyclohexyl)-1-propanols represented by the following general formula (I):

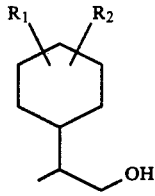

wherein $R_1$ and $R_2$ individually represent a group selected from the members consisting of methyl-, ethyl-, n-propyl-, i-propyl-, t-butyl-, and sec-butyl groups, provided that the total carbon atoms of the $R_1$ and $R_2$ groups are 4 to 7; either $R_1$ and $R_2$ is a hydrogen atom, with the other being a cyclohexyl group; or $R_1$ and $R_2$ together form a hexamethylene ring together with 2 carbon atoms in the cyclohexane ring.

Another object of this invention is to provide a process for preparing such 2-(alkyl-cyclohexyl)-1-propanols.

Still another object of this invention is to provide a perfumery composition comprising such a 2-(alkyl-cyclohexyl)-1-propanol.

Other objects, features and advantages of the invention will hereinafter become more readily apparent from the following description.

DETAILED DESCRIPTION OF THE INVENTION AND PREFERRED EMBODIMENTS

Given as specific examples of 2-(alkyl-cyclohexyl)-1-propanols of formula (I) are 2-(2-methyl-5-isopropyl-1-cyclohexyl)-1-propanol, 2-(2,5-di-isopropyl-1-cyclohexyl)-1-propanol, 2-(2,4- or 3,5-di-isopropyl-1-cyclohexyl)-1-propanol, 2-(2- or 4-cyclohexyl-1-cyclohexyl)-1-propanol, 2-(1- or 2-decaryl)-1-propanol, and the like.

The compounds of this invention can be prepared according to the following process:

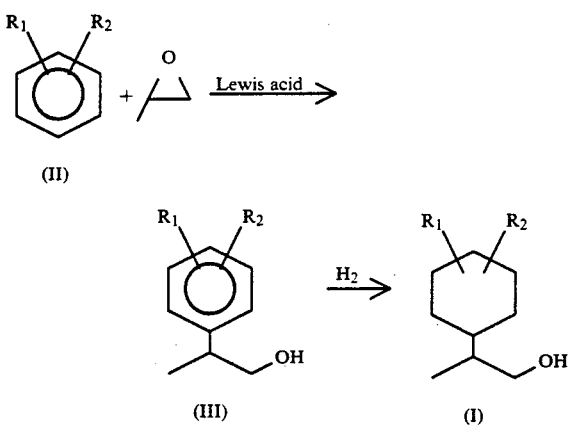

First, according to a conventional reaction [for example, Milstein; *J. Heterocycle. Chem.*, 5, 337 (1968)], an aromatic compound (II) is reacted with propylene oxide in the presence of a Lewis acid such as aluminum chloride, boron trifluoride, or the like to produce an intermediary alcohol (III). Aromatic compounds (II) which can be used in the above reaction include, for example, p-cymene, p- or m-diisopropylbenzene, diphenyl, tetralin, and the like. The amount of aromatic compound (II) is 1 to 10 equivalents per propylene oxide, with the particularly preferable amount being greater than 2 equivalents. The amount of Lewis acid is 1 to 2 equivalents per propylene oxide, with the particularly preferable amount being 1 to 1.5 equivalents. The reaction is carried out at a temperature between −60° to 0° C., preferably below −20° C.

In the next step, the compound of this invention (I) is prepared by the hydrogenation reaction of the aromatic ring of intermediary alcohol (III). Any conventional method which is applicable to the hydrogenation of aromatic rings can be employed for this reaction. For example, methods employing platinum oxide, Raney nickel, ruthenium carbon, or the like are used. The hydrogenation reaction using a metallic catalyst can be carried out in the absence of solvent. This reaction, however, can be carried out in the presence of a solvent; for example, a saturated hydrocarbon such as n-hexane or the like, or an alcohol such as methanol, ethanol, or the like. The amount of catalyst to be used is 1 to 10% by weight based on the amount of the intermediate (III). The hydrogen pressure in the reaction is between 20 and 150 atm. The reaction temperature depends upon the types of the compounds involved, although the generally applicable temperature is between 80° to 200° C. In order to shorten the reaction time and to reduce the production of by-products, the preferable reaction temperature is 100° to 150° C. The compound (I) of this invention can be obtained by evaporating the solvent and the like from the hydrogenated product, followed by vacuum distillation, recrystallization, and the like procedure.

The compound (I) of this invention thus prepared exists as a mixture of isomers resulting from the reaction of an aromatic compound and propylene oxide as well as stereoisomers resulting from the hydrogenation reaction. Fragrances of isomers are generally considered to be slightly different from each other. If necessary, these isomers are isolated from each other by conventional methods such as high pressure liquid chromatography, or the like. When using the compound (I) of this invention as a fragrance, however, it is usually unnecessary to isolate the isomers.

The compound (I) of this invention can provide a woody, floral odor when formulated into a perfume in an amount of 1 to 10% by weight.

Since 2-(alkyl-cyclohexyl)-1-propanols of the formula (I) of this invention possess a long-lasting, woody, floral odor, they can be widely used as perfumery materials such as perfumes, soaps, shampoos, aromatic goods, detergents, and the like.

Other features of the invention will become apparent in the course of the following description of the exemplary embodiments which are given for illustration of the invention and are not intended to be limiting thereof.

EXAMPLES

Example 1

Synthesis of 2-(1- or 2-decaryl)-1-propanol

Into a mixed solution of 325 ml (2.4 mol) of tetralin, 213 g (1.6 mol) of aluminum chloride, and 200 ml of methylene chloride was charged dropwise a mixture of 325 ml (2.4 mol) of tetralin and 112 ml (1.6 mol) of propylene oxide at −50° C. over 4 hours. The mixture thus obtained was stirred for 2 hours at −50° C. To this reaction mixture 1 liter of water was added to dissolve deposited salts and to separate the water and organic layers. Then, 300 ml of 5% aqueous solution of sodium hydroxide was added to the organic layer, followed by heating under reflux for 2 hours. After removing the water layer, the resulting residue was washed with water and dried over anhydrous magnesium sulfate to eliminate the solvent. The residue thus obtained was distilled under vacuum to produce 181 g (0.95 mol) of an alcoholic mixture as a fraction with a boiling point of 117° C. at 0.35 mmHg at a yield of 59%. Capillary gas chromatography analysis of this product indicated major component peaks at 62% and 34%.

| Elemental Analysis (As $C_{13}H_{18}O$) | | |
| --- | --- | --- |
| Calculated (%) | C: 82.06 | H: 9.53 |
| Measured (%) | C: 82.18 | H: 9.39 |

MS (relative intensity) [direct introduction]
190 (M+, 22), 159 (100), 131 (25),
117 (21), 91 (8)
IR (neat, cm$^{-1}$) [mixture]
3368, 2932, 1458, 1026, 772
$^1$H-NMR (Solvent: CDCl$_3$, Internal standard: TMS, δ) [mixture]

-continued 7.20–6.90 (3H, m), 3.66 (2H, t, J=6.0Hz),
2.90–2.60 (5H, m), 1.90–1.65 (4H, m),
1.55–1.35 (1H, m), 1.24 (3H, d, J=7.0Hz)

A mixture of 181 g (0.95 mol) of this alcoholic mixture and 18 g of 5% ruthenium carbon dry powder (manufactured by Nippon Engerhard Co., Ltd.), as a catalyst, was placed in a 300 ml autoclave. After replacing the internal atmosphere with hydrogen, the autoclave was heated to raise the internal temperature at an initial hydrogen pressure of 100 kg/cm². After 30 minutes following the start of heating, the reaction temperature reached 110° C. The reaction proceeded at this temperature for 6 hours, whereupon hydrogen absorption terminated. After cooling the reaction mixture, the pressure was restored to normal and the catalyst was separated by filtration. The filtrate was distilled under vacuum to obtain 139 g (0.71 mol) of the target alcohol isomers as a fraction having a boiling point range of 98.7° to 100° C. at 0.3 mmHg at a hydrogenation reaction yield of 73%. Capillary gas chromatography analysis of this product indicated major component peaks at 54%, 19%, and 15%. These compounds imparted a woody, floral, and slightly amber-like odor.

| Elemental Analysis (As $C_{13}H_{24}O$) | | |
| --- | --- | --- |
| Calculated (%) | C: 79.53 | H: 12.32 |
| Measured (%) | C: 79.34 | H: 12.48 |

MS (relative intensity) [major component at 54% peak]
178 (M+-H$_2$O, 19), 137 (19), 136 (55),
135 (100), 121 (20), 95 (81), 94 (26), 81 (81),
79 (22), 67 (41)
IR (neat, cm$^{-1}$) [mixture]
3336, 2924, 1450, 1030,
NMR (Solvent: CDCl$_3$, Internal standard: TMS, δ) [mixture]
3.75–3.40 (2H, m), 0.91 (3H, d, J=7Hz),
1.80–0.70 (19H, m)

EXAMPLE 2

Synthesis of 2-(2-methyl-5-isopropyl-1-cyclohexyl)-1-propanol

The reaction was carried out in the same manner as in Example 1, except that 375 ml (2.4 mol) of p-cymene was used instead of tetralin. After processing the reaction product in the same way as in Example 1 and through distillation under vacuum, 176 g (0.91 mol) of aromatic alcohol isomers were obtained as a fraction having a boiling point of 100° C. at 0.45 mmHg at a yield of 57%.

| Elemental Analysis (As $C_{13}H_{20}O$) | | |
| --- | --- | --- |
| Calculated (%) | C: 81.20 | H: 10.48 |
| Measured (%) | C: 81.25 | H: 10.37 |

MS (relative intensity)
192 (M+, 24), 177 (4), 161 (100), 145 (4),
133 (11), 119 (28), 105 (15), 91 (11), 77 (5),
43 (19)
IR (neat, cm$^{-1}$)
3352, 2962, 1461, 1026, 819
NMR (Solvent: CDCl$_3$, Internal standard: TMS, δ)
7.15–6.90 (3H, m), 3.69 (2H, m), 3.23 (1H, sep, J=7Hz),
2.86 (1H, sep, J=7Hz), 2.31 (3H, s), 1.61 (1H, brs),
1.24 (3H, d, J=7Hz), 1.23 (6H, d, J=7Hz)

A mixture of 40 g (0.2 mol) of these alcohol isomers, 2 g of 5% ruthenium carbon, as a catalyst, and 20 ml of ethanol was placed in a 100 ml autoclave. After replacing the internal atmosphere with hydrogen, the autoclave was heated to raise the internal temperature at an initial hydrogen pressure of 120 kg/cm². After 1 hour following the start of heating, the reaction temperature reached 150° C. The reaction proceeded at this temperature for 3 days, whereupon hydrogen absorption terminated. After cooling the reaction mixture, the pressure was restored to normal and the catalyst was separated by filtration. The filtrate was distilled under vacuum to obtain 28 g (0.14 mol) of the target alcohol isomers as a fraction having a boiling point range of 116° to 117° C. at 0.3 mmHg at a hydrogenation reaction yield of 67%. Capillary gas chromatography analysis of this product indicated major component peaks at 50% and 31%. These compounds imparted a floral, waxy, and slightly woody odor.

| Elemental Analysis (As $C_{13}H_{26}O$) | | |
|---|---|---|
| Calculated (%) | C: 78.72 | H: 13.21 |
| Measured (%) | C: 78.88 | H: 13.11 |

MS (relative intensity) [major component at 50% peak]
180 ($M^+$-$H_2O$, 4), 138 (63), 137 (42),
123 (18), 109 (17), 95 (76), 83 (100), 81 (56),
69 (57), 55 (39)
IR (neat, $cm^{-1}$) [mixture]
3336, 2960, 2928, 1466, 1386, 1028
NMR (Solvent: $CDCl_3$, Internal standard: TMS, δ) [mixture]
3.80–3.65 (1H, m), 3.60–3.35 (1H, m), 2.00 (1H, m),
1.85–1.05 (11H, m), 1.02 (3H, d, J=7Hz),
1.00–0.75 (9H, d, J=7Hz)

EXAMPLE 3

2-(2,5-di-isopropyl-1-cyclohexyl)-1-propanol

The reaction was carried out in the same manner as in Example 1, except that 191 ml (0.9 mol) of p-diisopropylbenzene was used instead of tetralin. After processing the reaction product in the same way as in Example 1 and through distillation under vacuum, 60 g (0.27 mol) of aromatic alcohol isomers were obtained as a fraction having a boiling point range of 113.5° to 114.5° C. at 1.4 mmHg at a yield of 30%.

| Elemental Analysis (As $C_{15}H_{24}O$) | | |
|---|---|---|
| Calculated (%) | C: 81.76 | H: 10.98 |
| Measured (%) | C: 81.92 | H: 10.79 |

MS (relative intensity)
220 ($M^+$, 24), 189 (100), 161 (21), 147 (14),
133 (6), 131 (6), 119 (16), 105 (8), 91 (14),
43 (32)
IR (neat, $cm^{-1}$)
3346, 2962, 1464, 1026
NMR (Solvent: $CDCl_3$, Internal standard: TMS, δ)
7.22 (1H, d, J=8Hz), 7.07 (1H, d, J=8Hz),
7.04 (1H, s), 3.70 (2H, sep, J=7Hz), 3.36 (1H, m),
3.25 (1H, m), 2.86 (1H, sep, J=7Hz), 1.63 (1H, brs),
1.40–1.00 (15H, d, J=7Hz)

A mixture of 33 g (0.15 mol) of this alcoholic compound, 3 g of 5% ruthenium carbon, as a catalyst, and 110 ml of hexane was placed in a 300 ml autoclave. After replacing the internal atmosphere with hydrogen, the autoclave was heated to raise the internal temperature at an initial hydrogen pressure of 100 kg/cm². After 30 minutes following the start of heating, the reaction temperature reached 150° C. The reaction proceeded at this temperature for 17 hours, whereupon hydrogen absorption terminated. After cooling the reaction mixture, the pressure was restored to normal and the catalyst was separated by filtration. The filtrate was distilled under vacuum to obtain 12 g (0.05 mol) of the target alcoholic isomers as a fraction having a boiling point of 112° C. at 0.75 mmHg at a hydrogenation reaction yield of 33%. Capillary gas chromatography analysis of this product indicated major component peaks at 52% and 18%. These compounds imparted a weak woody, amber-like odor.

| Elemental Analysis (As $C_{15}H_{30}O$) | | |
|---|---|---|
| Calculated (%) | C: 79.58 | H: 13.36 |
| Measured (%) | C: 79.45 | H: 13.51 |

MS (relative intensity) [major component at 52% peak]
208 ($M^+$$H_2O$, 2), 183 (12), 165 (23),
123 (32), 111 (35), 109 (100), 95 (47), 83 (30),
81 (29), 69 (58)
IR (neat, $cm^{-1}$) [mixture]
3332, 2960, 2872, 1470, 1388, 1370, 1032
NMR (Solvent: $CDCl_3$, Internal standard: TMS, δ) [mixture]
3.80–3.60 (1H, m), 3.60–3.50 (1H, m),
2.05–0.60 (13H, m), 0.98 (6H, d, J=7Hz),
0.96 (3H, d, J=7Hz), 0.87 (3H, d, J=7Hz),
0.85 (3H, d, J=7Hz)

EXAMPLE 4

2-(2,4- or 3,5-di-isopropyl-1-cyclohexyl)-1-propanol

The reaction was carried out in the same manner as in Example 1, except that 1168 ml (6.2 mol) of m-diisopropylbenzene was used instead of tetralin. After processing the reaction product in the same way as in Example 1 and through distillation under vacuum, 900 g (4.1 mol) of aromatic alcohol isomers were obtained as a fraction having a boiling point range of 109° to 111° C. at 0.5 mmHg at a yield of 66%. Capillary gas chromatography analysis of this product indicated major component peaks at 60% and 28%.

| Elemental Analysis (As $C_{15}H_{24}O$) | | |
|---|---|---|
| Calculated (%) | C: 81.76 | H: 10.98 |
| Measured (%) | C: 81.65 | H: 11.07 |

MS (relative intensity) [major component at 60% peak]
220 ($M^+$, 8), 189 (100), 161 (9), 147 (20),
133 (10), 119 (29), 105 (13), 91 (21), 43 (48),
41 (22)
IR (neat, $cm^{-1}$) [mixture]
3368, 2964, 1464, 1032,
NMR (Solvent: $CDCl_3$, Internal standard: TMS, δ)
7.20–6.85 (3H, m), 3.70 (2H, d, J=7Hz),
3.30 (2H, m), 2.90 (1H, d, J=7Hz), 1.4–1.1 (16H, m)

A mixture of 800 g (3.63 mol) of these alcohol isomers and 32 g of 5% ruthenium carbon (containing 50% water), as a catalyst, was placed in a 1-liter autoclave. After replacing the internal atmosphere with hydrogen, the autoclave was heated to raise the internal temperature at an initial hydrogen pressure of 100 kg/cm². After 1 hour following the start of heating, the reaction temperature reached 150° C. The reaction proceeded at this temperature for 10 days, whereupon hydrogen absorption terminated.

After cooling the reaction mixture, the pressure was restored to normal and the catalyst was separated by filtration. The filtrate was distilled under vacuum to obtain 456 g (2.0 mol) of an alcoholic isomer mixture as a fraction having a boiling point of 108° C. at 0.8 mmHg at a hydrogenation reaction yield of 55%. Capillary gas chromatography analysis of this product indicated major component peaks at 31%, 19%, 7.3%, and 6.3%. These compounds imparted a weak woody, amber-like, floral odor.

| Elemental Analysis (As $C_{15}H_{30}O$) | | |
|---|---|---|
| Calculated (%) | C: 79.58 | H: 13.36 |
| Measured (%) | C: 79.49 | H: 13.51 |

MS (relative intensity) [major component at 31% peak]
208 ($M^+$-$H_2O$, 2), 189 (11), 183 (12),
165 (22), 152 (16), 123 (34), 111 (39), 109 (100),
95 (48), 83 (35), 81 (33), 69 (63)
IR (neat, $cm^{-1}$) [mixture]
3328, 2960, 1468, 1030
NMR (Solvent: $CDCl_3$, Internal standard: TMS, δ) [mixture]
3.75–3.55 (1H, m), 3.55–3.35 (1H, m),
2.0–0.50 (28H, m)

EXAMPLE 5

2-(2- or 4-cyclohexyl-1-cyclohexyl)-1-propanol

Into a mixed solution of 250 ml (1.6 mol) of biphenyl, 216 g (1.6 mol) of aluminum chloride, and 500 ml of methylene chloride was charged dropwise a mixture of 113 ml (1.6 mol) of propylene oxide and 500 ml of methylene chloride at $-30°$ C. over 2 hours. The mixture thus obtained was stirred for 2 hours at $-30°$ C. To this reaction mixture 1 liter of water was added to separate the water and organic layers. Then, 250 ml of 5% aqueous solution of sodium hydroxide was added to the organic layer, followed by heating under reflux for 2 hours. After removing the water layer, the resulting residue was washed with water and dried over anhydrous magnesium sulfate to eliminate the solvent and to obtain 320 g of a crude reaction product. A mixture of 300 g of this crude product and 15 g of 5% ruthenium carbon (containing water) was placed in a 500 ml autoclave. After replacing the internal atmosphere with hydrogen, the autoclave was heated to raise the internal temperature at an initial hydrogen pressure of 120 $kg/cm^2$. After 30 minutes following the start of heating, the reaction temperature reached 150° C. The reaction proceeded at this temperature for 3 days, whereupon hydrogen absorption terminated. After cooling the reaction mixture, the pressure was restored to normal and the catalyst was separated by filtration. The filtrate was distilled under vacuum to obtain 68 g (0.30 mol) of the target alcohol isomer mixture as a fraction having a boiling point range of 136° to 143° C. at 1.8 mmHg at a total reaction yield of 19%.

Capillary gas chromatography analysis of these compounds indicated major component peaks at 25%, 21%, and 21%. These compounds imparted a waxy, floral, and slightly woody odor.

| Elemental Analysis (As $C_{15}H_{28}O$) | | |
|---|---|---|
| Calculated (%) | C: 80.29 | H: 12.58 |
| Measured (%) | C: 80.46 | H: 12.43 |

MS (relative intensity) [major component at 25%, 21% peaks]
206 ($M^+$-$H_2O$, 5), 187 (20), 165 (28),
141 (15), 123 (83), 109 (44), 95 (29), 83 (100),
81 (100), 81 (92), 55 (85)
IR (neat, $cm^{-1}$) [mixture]
3348, 2928, 1452, 1026
NMR (Solvent: $CDCl_3$, Internal standard: TMS, δ) [mixture]
3.8–3.2 (2H, m), 2.2–0.7 g (26H, m)

EXAMPLE 6

Perfumery Preparation for Herbal Shampoo

| <Formulation> | (% by weight) |
|---|---|
| Lemon oil California | 100 |
| Orange oil Valencia | 50 |
| Lavender oil Mont Blanc 40/42 | 40 |
| Peppermint oil Mitwestscotti | 10 |
| Cis-3-hexenyl acetate | 1 |
| Cis-3-hexenol | 2 |
| p-tert-Butylcyclohexyl acetate | 30 |
| Geraniol extra | 100 |
| Citonellol extra | 40 |
| Phenylethyl alcohol | 100 |
| Lilial *1 | 30 |
| Lyral *2 | 50 |
| 4-Acetoxy-3-pentyltetrahydropyran | 20 |
| Hexylcinnamic aldehyde | 235 |
| Galaxolide 50 DEP *3 | 60 |
| Benzoin resinoide | 20 |
| Vanillin | 1 |
| Vetiver oil Java | 10 |
| Raspberry ketone *4 | 1 |

*1 Lilial: Tradename, produced by Givaudan Co.; p-tert-butyl-α-methylhydrocinnamic aldehyde
*2 Liral: Tradename, produced by IFF Co.; 4-(4-hydroxy-4-methylpentyl)-3-cyclohexene-1-carboxy aldehyde
*3 Galaxolide 50 DEP: Tradename, produced by IFF Co.; 50% diethylphthalate solution of 1,3,4,6,7,8-hexahydro-4,6,6,7,8,8-hexmethylcyclopenta-γ-2-benzopyran
*4 Raspberry ketone: 4-(p-hydroxyphenyl)-2-butanone To 900 parts by weight of the above composition 100 parts by weight of 2-(2,4- or 3,5-di-isopropyl-1-cyclohexyl)-1-propanol was added to obtain a perfumery composition for a herbal shampoo with a strong minty fragrance of a great volume.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent is:

1. 2-(alkyl-cyclohexyl)-1-propanols represented by the following general formula (I):

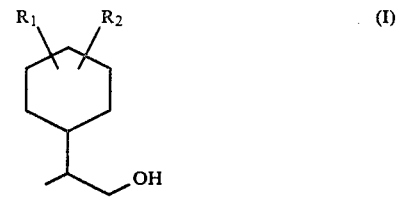

wherein $R_1$ and $R_2$ individually represent a group selected from the members consisting of methyl-, ethyl-, n-propyl-, i-propyl-, t-butyl-, and sec-butyl groups, provided that the total carbon atoms of the $R_1$ and $R_2$ groups are 4 to 7; either $R_1$ and $R_2$ is a hydrogen atom, the other being a cyclohexyl group; or $R_1$ and $R_2$ together form a hexamethylene ring together with 2 carbon atoms in the cyclohexane ring.

2. A perfumery composition, comprising at least a top, middle and base note, said base note comprising a compound of claim 1.

3. The perfumery composition of claim 2, wherein said base note is present in amounts of 1–10%, by weight.

4. The perfumery composition of claim 2, wherein said perfumery composition is in the form of a perfume, soap, shampoo or detergent.

* * * * *